United States Patent [19]

Bragulla et al.

[11] Patent Number: 6,042,818
[45] Date of Patent: Mar. 28, 2000

[54] FILM-BUILDING AGENT USEFUL TO PROTECT AGAINST INFECTIONS

[75] Inventors: Siegfried Bragulla, Monheim, Germany; Gilbert Bardoneschi, Bassu, France; Juergen Beckmann-Toussaint, Bonn, Germany

[73] Assignee: Henkel Ecolab GmbH & Co. OHG, Duesseldorf, Germany

[21] Appl. No.: 09/230,702
[22] PCT Filed: Jul. 21, 1997
[86] PCT No.: PCT/EP97/03922
§ 371 Date: Jan. 29, 1999
§ 102(e) Date: Jan. 29, 1999
[87] PCT Pub. No.: WO98/04136
PCT Pub. Date: Feb. 5, 1998

[30] Foreign Application Priority Data

Jul. 30, 1996 [DE] Germany ............................ 196 30 622
Feb. 24, 1997 [DE] Germany ............................ 197 07 081

[51] Int. Cl.$^7$ .................................................. A61K 31/755
[52] U.S. Cl. ..................... 424/78.07; 424/78.05; 424/405; 424/407
[58] Field of Search .................... 424/404, 407, 424/78.07, 78.05, 405; 119/14.02; 514/635, 772.4

[56] References Cited

U.S. PATENT DOCUMENTS 4,466,959  8/1984  Lauermann et al. .................... 424/150
5,017,369  5/1991  Marhevka ................................. 424/78

FOREIGN PATENT DOCUMENTS 0 090 205   10/1983   European Pat. Off. .
0 212 866    3/1987   European Pat. Off. .
42 25 626    2/1983   Germany .
42 41 079    6/1994   Germany .
WO81/01516   6/1981   WIPO .
WO94/23581  10/1994   WIPO .

OTHER PUBLICATIONS

Toxicoligic Studies of Alkylphenol Polyoxyethylene Surfactants–Toxicology and Applied Pharmacology 14, pp. 315–334, 1969.
Bundestagsdrucksache 13/3181–13, Wahlperiode.
Environmental Toxicology and Chemistry, vol. 15, No. 3, pp. 241–248, 1996, Setac.
CEFIC Press Statement "Environmental Estrogen and Endocrine Modulators", Apr. 29th, 1996.

*Primary Examiner*—Thurman K. Page
*Assistant Examiner*—Amy E Pulliam
*Attorney, Agent, or Firm*—W. C. Jaeschke; Glenn E.J. Murphy

[57] ABSTRACT

A composition and process for protection against infection wherein the composition contains a) 10 to 100 g/l of polyvinyl alcohol polymers or copolymers having molecular weights from 18,000 to 200,000 as the film forming component, b) 0.2 to 3 g/l of iodine in the form of polyvinyl pyrrolidone iodine and/or 5 to 50 g/l of chlorhexidine as the disinfecting agent, and c) 2 to 50 g/l of ether carboxylic acids corresponding to formula $R-(OC_2H_4)_n-OCH_2-COOH$, where R is an alkyl group containing 4 to 10 carbon atoms and n is a number of 2 to 8.

12 Claims, No Drawings

FILM-BUILDING AGENT USEFUL TO PROTECT AGAINST INFECTIONS

This application is a 321 of PCT/EP97/03922, filed Jul. 7, 1997.

BACKGROUND OF THE INVENTION

1. Field of the Invention

This invention relates to a film-forming preparation for protection against infections which is particularly suitable for protecting teats and udders of cattle, sheep and goats against infections after milking.

Nowadays, cattle, sheep and goats are mainly milked by automatic milking techniques. The animals, which have been bred over many years for high milk production, are extremely susceptible to infection in the region of their mammary glands and udders. This susceptibility to infection is increased by the heavy stressing which the teats undergo during milking and by environmental factors to which the teats are constantly exposed, such as wind, rain and sunshine.

As a result of this constant stressing of their teats, the animals frequently develop udder inflammations which are described in the literature as "subclinical" or "clinical" mastitis. Depending on the level of infection of the affected part of the udder, there is a slight to drastic increase in somatic cells in the milk. The increase in somatic cells in the milk beyond the level of healthy udders (200,000 cells per ml) is undesirable because it affects the quality of the milk for the subsequent processing steps or, in extreme cases, makes the milk unfit for consumption. A drastic increase in somatic cells in the milk is often accompanied by fever (clinical mastitis) and can even result in the loss of the animal through enforced slaughter.

One of the causes of such infections is the penetration of udder-pathogenic bacteria such as, for example, *Pseudomonas aeruginosa, Escherichia coli, Streptococcus uberis, Streptococcus dysagalactiae, Streptococcus agalactiae, Staphylococcus aureus, Enterococcus hirae.*

The risk of udder infection is at its greatest immediately after milking when the nipple duct is open so that bacteria from the environment around the udder are able to migrate into the nipple duct and to cause infections.

In order to avoid or reduce the risk of infection, the teats of the milked animals are treated with udder "dips" after each milking. The treatment is carried out either by dipping the teats in or spraying them with the disinfecting solution. As a result of this measure, the bacteria present on the udder/teat skin are destroyed in 10 minutes, thus reducing the risk of infection through the open nipple duct.

Unfortunately, the disadvantage of using udder dips is that the nipple duct is open for up to 60 minutes after milking. However, commercial dips are of such low viscosity that they mechanically close the nipple duct for only a short time (about 10 minutes) by forming droplets at the ends of the teats. This protection of the teats is removed again after a short time by drying of the preparation in the air or by rubbing off of the preparation from the ends of the teats when the animals lie down. Accordingly, the teats are again susceptible to infection by pathogenic bacteria through the open nipple duct. Another disadvantage of known products lies in the very high concentration of disinfecting agent in the preparations which is required to achieve a disinfecting effect in the short contact time described.

2. Discussion of Related Art

Concentrations of free iodine of 2,500 to 10,000 ppm are normally used to achieve adequate germ destruction levels (3.0 log stages) on the udder/teat skin. Iodine concentrations as high as these lead to a corresponding increase in the iodine content of the milk which should be avoided in the interests of human health.

Further disadvantages of such preparations lie in the use of nonylphenol ethoxylates as iodine carriers (nonoxinol iodine). Earlier toxicological studies point to the risk to health posed by nonoxinols as a residue in foods. The danger of "myocordial necroses" is described in the studies of Smith and Calandra (Toxicological Studies of Alkylphenol Polyoxyethylene Surfactants—Toxicology and Applied Pharmacology 14, 315–334, 1969). The latest toxicological discussions relate to the estrogenic effects of such substances (Bundestagsdrucksache 13/3181-13, Wahlperiode// Environmental Toxicology and Chemistry, Vol. 15, No. 3, pp 241–248, 1996, Setac//CEFIC Press Statement "Environmental Estrogen and Endocrine Modulators", Apr. 29, 1996).

For example, EP-A-90 205 describes an udder care and teat disinfecting preparation for dairy cattle which is formulated for application as a high-viscosity aqueous emulsion and which contains inter alia 800 to 1,200 ppm of iodine in the form of a disinfecting iodine complex. Adducts of iodine with polyglycol ethers or with polyvinyl pyrrolidone may be used as the disinfecting iodine complex.

WO 94/23581 describes teat disinfectants which are free from many of the disadvantages mentioned above. They contain a film-forming component consisting of polyvinyl alcohol, a polymeric thickener and an antimicrobial nonionic iodine complex. The nonionic iodine complex may be selected, for example, from adducts of iodine with polyethylene glycol, polypropylene glycol or copolymers thereof. Alcoholates, phenolates and carboxylates may be used as polymerization initiating molecules. According to the Examples, nonylphenol ethoxylates are used as iodine carriers.

The problem addressed by the present invention was to provide a film-forming preparation for protecting the teats and udders of dairy cattle against infection which would not require the ecologically and toxicologically unsafe nonylphenol ethoxylates. Suitable toxicologically favorable alternatives are, on the one hand, chlorhexidine and, on the other hand, iodine in the form of polyvinyl pyrrolidone iodine. However, if an attempt is made to replace the nonylphenol ethoxylate iodine in the film formers according to WO 94/23581 by these more favorable disinfecting agents, either firmly adhering films which cannot be removed in a reasonable time are obtained, depending on the formulation, or the films remain moist and tacky so that they are either rubbed off or lead to heavily soiled udders by attracting dirt when the cattle lie down. Accordingly, another problem addressed by the invention was to provide an alternative film-forming preparation that would form firmly adhering, dry films which would protect the teat skin and which would be able to be removed in a short time, for example in about 10 to about 60 seconds, by exposure to moisture.

DESCRIPTION OF THE INVENTION

The problem stated above has been solved by a film-forming preparation for protection against infections which contains a film-forming component and one or more disinfecting agents, characterized in that it contains a) 10 to 100 g/l of polyvinyl alcohol polymers or copolymers with molecular weights in the range from 18,000 to 200,000 as the film-forming component, b) 0.2 to 3 g/l of iodine in the form of polyvinyl pyrrolidone iodine and/or 0.5 to 5 g/l of chlorhexidine as the disinfecting agent and c) 2 to 50 g/l of ether carboxylic acids corresponding to the general formula R—$(OC_2H_4)_n$—$OCH_2$—$COOH$, where R is an alkyl group containing 4 to 10 carbon atoms and n is a number of 2 to 8.

It has surprisingly been found that a film-forming preparation with the necessary film properties is only obtained through the presence of the ether carboxylic acids. Suitable ether carboxylic acids are known, for example, from DE-A-42 25 626 which describes their use as disinfecting agents. Ether carboxylic acids such as these can be prepared by initially ethoxylating the corresponding alkanols with the substituent R and reacting the ethoxylates with chloroacetic acid. Since mixtures of ethoxylation products differing in their degrees of ethoxylation, rather than pure substances with a defined value for n, are obtained in the ethoxylation step, the ether carboxylic acids are generally corresponding mixed products. Ether carboxylic acids in which the alkyl group R contains 4 to 8 carbon atoms are preferably used. The film former preferably contains 5 to 20 g/l of ether carboxylic acids.

Polyvinyl alcohol polymers or copolymers are used as the film-forming component. In order to obtain favorable film forming properties, the molecular weights of these polymers, which can be determined for example by gel permeation chromatography, should be in the range from 18,000 to 200,000 and preferably in the range from 50,000 to 150,000. The film-forming component is preferably used in quantities of 30 to 50 g/l.

To adjust its viscosity, the preparation preferably contains from 1,000 to 10,000 mg/l of a thickener. The concentration of the thickener is preferably from 3,000 to 6,000 mg/l. Particularly suitable thickeners are those which have been approved as food additives, including for example xanthan gum, carboxymethyl cellulose or even alginates which may be used either individually or in the form of mixtures with one another. If mixtures of different thickeners are used, the concentration figures mentioned above apply to the total concentration.

The preparation contains polyvinyl pyrrolidone iodine and/or chlorhexidine as the disinfecting agent. Polyvinyl pyrrolidone iodine is particularly preferred. Polyvinyl pyrrolidone iodine is widely used as a disinfectant. It consists of an addition complex of molecular iodine and, in some cases, even triiodide ions with polyvinyl pyrrolidone. This disinfecting agent is preferably used in such a quantity that the iodine content of the preparation is in the range from about 0.4 to about 1.5 g/l and, more particularly, in the range from about 0.5 to about 1 g/l.

Chorhexidine, which may be used as an alternative to or together with polyvinyl pyrrolidone iodine, is also known from the prior art as a disinfecting agent. It is preferably used in the form of the gluconate. The concentration of chlorhexidine is in the range from about 5 to about 50 g/l and preferably in the range from about 10 to about 30 g/l.

The preparation may additionally contain typical skin-care ingredients for use on udders in the usual quantities. Examples of such additional ingredients are glycerol and alantoin.

The preparations according to the invention are ready to use and represent an alternative to commercially available preparations which can also have film-forming properties, but in which nonylphenol ethoxylates are used as iodine carriers or in which a ready-to-use solution has to be prepared from several components before use. The combination according to the invention of polyvinyl alcohol as a film-forming component, polyvinyl pyrrolidone iodine and/or chlorhexidine as a disinfecting agent and the ether carboxylic acids for adjusting the film-forming properties leads to a preparation which fully satisfies the requirements stated above.

If desired, the preparation according to the invention may additionally contain about 1 to about 20 g/l of one or more surfactants selected from anionic or nonionic surfactants. Suitable anionic surfactants are, for example, alkyl sulfates or sulfonates and alkyl benzenesulfonates while suitable nonionic surfactants are, in particular, fatty alcohol ethoxylates. The surfactant concentration is preferably in the range from about 2 to about 10 g/l.

Finally, the present invention relates to the use of the preparation described above for protecting the teats and udders of cattle, sheep and/or goats against infections of the type which can occur, in particular, after milking and above all after automatic milking. The preparation is used, for example, by immersing the teats or udders of cattle, sheep or goats in or spraying them with the preparation after milking. The preparation is preferably used by dipping the teats in the preparation after milking.

The effect of the use according to the invention is that, after application to udders or teats, the preparation forms a visible, mechanically strong film. "Visible" in this context means that the film can be seen with the naked eye. "Mechanically strong" means that the film is continuous and can be peeled off in coherent pieces, at least from smooth surfaces. On the one hand, the film mechanically closes the nipple duct and, on the other hand, allows the disinfecting agent a long contact time. As a result, the quantity in which the disinfecting agent is used can be significantly reduced by comparison with conventional preparations. This reduces the risk of contamination of the milk with the disinfectant at the next milking. Despite the reduced in-use concentration, the udder/teat skin is adequately disinfected against pathogenic bacteria within 10 minutes by virtue of the film-forming effect. Before the next milking, the protective film can be removed very easily from the udder/teat skin in a short time, for example in 10 to 60 seconds, using moist cloths or other water-based steeping preparations. This is another advantage of the preparations according to the invention over those according to WO 94/23581, according to which complete removal of the film takes more than 1 minute, for example about 5 minutes. Accordingly, the invention provides toxicologically improved preparations which afford the teats and udders of milked animals safe protection against re-infection.

EXAMPLES

A disinfecting test was carried out in accordance with the procedure laid down by the National Mastitis Council, USA (Protocol A). After a contact time of 10 minutes at 20° C., a destruction rate of more than 3 powers of ten was determined (test germ: Staphylococcus aureus, destruction rate 3.67 common logarithmic steps).

| Formulation used (% by weight): | |
| --- | --- |
| Deionized water | 88.3% |
| Alkyl benzenesulfonic acid | 0.20% |
| Polyvinyl alcohol copolymer | 4.00% |
| Xanthan gum | 0.45% |
| Glycerol | 5.05% |
| Polyvinyl pyrrolidone iodine (10% iodine) | 1.00% |
| Caprylic ether carboxylic acid | 1.0% |

Table 1 shows that, where polyvinyl alcohol is used as the film forming component and polyvinyl pyrrolidone iodine or chlorhexidine as the disinfecting component, the films obtained are either difficult to remove or form tacky coatings, depending on the other ingredients used by contrast, Table 2—with the aid of Examples according to the invention—shows that only the addition of various alkyl ether carboxylic acids leads to the dry and strong, but readily removable films required.

TABLE 1

Comparison formulations 1 to 12 (% by weight) film formation

| | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| Water of condensation | Balance to 100 | Balance to 100 | Balance to 100 | Balance to 100 | Balance to 100 | Balance to 100 | Balance to 100 | Balance to 100 | Balance to 100 | Balance to 100 | Balance to 100 | Balance to 100 |
| Xanthan gum | 0.2–0.6 | 0.2–0.6 | 0.2–0.6 | 0.2–0.6 | 0.2–0.6 | 0.2–0.6 | 0.2–0.6 | 0.2–0.6 | 0.2–0.6 | 0.2–0.6 | 0.2–0.6 | 0.2–0.6 |
| Polyvinyl alcohol copolymer (molecular weight 50,000–150,000) | 0.5–5 | 0.5–5 | 0.5–5 | 0.5–5 | 0.5–5 | 0.5–5 | 0.5–5 | 0.5–5 | 0.5–5 | 0.5–5 | 0.5–5 | 0.5–5 |
| Polyvinyl pyrrolidone iodine (10% iodine) | 0.5–3 | 0.5–3 | 0.5–3 | 0.5–3 | 0.5–3 | — | — | — | — | — | 0.5–3 | — |
| Alkyl benzenesulfonic acid | 0.1–0.3 | 0.1–0.3 | 0.1–0.3 | 0.1–0.3 | 14 | 1–4 | 0.1–0.3 | 0.1–0.3 | 0.1–0.3 | 0.1–0.3 | 0.1–0.3 | 0.1–0.3 |
| $C_{12-18}$ fatty alcohol + 8 moles EO | 1–4 | — | — | — | — | — | 1–4 | — | — | — | — | — |
| Oleyl-cetyl alcohol + 5 moles EO | — | 1–4 | — | — | — | — | — | 1–4 | — | — | — | — |
| Oleyl-cetyl alcohol + 10 moles EO | — | — | 1–4 | — | — | — | — | — | 1–4 | — | — | — |
| $C_{12-18}$ fatty alcohol + 6 moles EO | — | — | — | 1–4 | — | — | — | — | — | 1–4 | — | — |
| Chlorhexidine digluconate | — | — | — | — | — | 0.5–3 | 0.5–3 | 0.5–3 | 0.5–3 | 0.5–3 | — | 0.5–3 |

The disadvantage of these formulations (Nos. 1 to 12) lies in their poor film formation. The combination of PVP iodine or chlorhexidine digluconate with a film former, such as PVA, gives strong films on the teat/udder skin which cannot be removed, even with water, in the time available (formulations 11+12). The addition of typical anionic or nonionic surfactants leads to tacky residues on the teat/udder skin. Accordingly, strong dry films are not formed. These tacky films are rubbed off too soon when the cattle lie down and, accordingly, do not afford the teats long-term protection. Another disadvantage is that soil/dirt residues adhere to the tacky film.

TABLE 2

Formulations according to the invention (% by weight): film formation

| | 13 | 14 | 15 | 16 |
| --- | --- | --- | --- | --- |
| Water of condensation | Balance to 100 | Balance to 100 | Balance to 100 | Balance to 100 |
| Xanthan gum | 0.2–0.6 | 0.2–0.6 | 0.2–0.6 | 0.2–0.6 |
| Polyvinyl alcohol copolymer (molecular weight 50,000–150,000 | 0.5–5 | 0.5–5 | 0.5–5 | 0.5–5 |
| Glycerol | 3–10 | 3–10 | 3–10 | 3–10 |
| Polyvinyl pyrrolidone iodine (10% iodine) | 0.5–3 | 0.5–3 | — | — |
| Chlorhexidine digluconate | — | — | 0.5–3 | 0.5–3 |
| Alkyl ether carboxylic acid (capryl) | 0.5–2 | — | 0.5–2 | — |
| Mixture of capryl + butyl ether carboxylic acid | — | 0.5–2 | — | 0.5–2 |

It has surprisingly been found that the use of carboxylic acids corresponding to the general formula $R(OC_2H_4)_nOCH_2COOH$ in combination with PVA as the film-forming component and PVP iodine or chlorhexidine digluconate as the disinfecting component leads to the formation of firmly adhering, dry films which protect the teat/udder skin. These films can be removed very easily from the teat/udder skin in a short time (10 to 60 seconds) using moist cloths or other water-based steeping preparations (formulations 13 to 16).

We claim:

1. A film-forming composition for protection against infections containing a film-forming component and one or more disinfecting agents, said composition comprising
   a) a film-forming component comprising 10 to 100 g/l of polyvinyl alcohol polymers or copolymers thereof having a molecular weight from 18,000 to 200,000,
   b) a disinfecting agent comprising 0.2 to 3 g/l of iodine in the form of polyvinyl pyrrolidone iodine or 5 to 50 g/l of chlorhexidine, and
   c) 2 to 50 g/l of ether carboxylic acids corresponding to formula R—$(OC_2H_4)_n$—$OCH_2$—COOH, wherein R is an alkyl group containing 4 to 10 carbon atoms and n is a number of 2 to 8.

2. A film-forming composition in claim 1 wherein said ether carboxylic acids contain 4 to 8 carbon atoms in the alkyl group R.

3. A film-forming composition as in claim 1 further containing 1 to 10 g/l of a thickening agent.

4. A film-forming composition as in claim 3 wherein said thickening agent is selected from the group consisting of xanthan gum, carboxymethyl cellulose and alginates.

5. A film-forming composition as in claim 1 further containing 1 to 20 g/l of one or more surfactants selected from anionic and nonionic surfactants.

6. The process of protecting the teats and udders of cattle, sheep or goats against infection after milking, comprising contacting said teats or udders with a film-forming composition containing a) a film-forming component comprising 10 to 100 g/l of polyvinyl alcohol polymers or copolymers thereof having a molecular weight from 18,000 to 200,000, b) a disinfecting agent comprising 0.2 to 3 g/l of iodine in the form of polyvinyl pyrrolidone iodine or 5 to 50 g/l of chlorhexidine, and c) 2 to 50 g/l of ether carboxylic acids corresponding to formula $R-(OC_2H_4)_n-OCH_2-COOH$, wherein R is an alkyl group containing 4 to 10 carbon atoms and n is a number of 2 to 8.

7. A process as in claim 6 wherein said ether carboxylic acids contain 4 to 8 carbon atoms in the alkyl group R.

8. A process as in claim 6 wherein said composition contains 1 to 10 g/l of a thickening agent.

9. A process as in claim 8 wherein said thickening agent is selected from the group consisting of xanthan gum, carboxymethyl cellulose and alginates.

10. A process as in claim 6 wherein said composition further contains 1 to 20 g/l of one or more surfactants selected from anionic and nonionic surfactants.

11. A process as in claim 6 wherein said contacting step is conducted by dipping in or spraying said teats or udders with said composition after milking said cattle, sheep or goats.

12. A process as in claim 11 wherein after said contacting step said composition forms a visible and mechanically strong film on said teats or udders.

* * * * *